United States Patent
Erkens et al.

(10) Patent No.: US 10,702,461 B2
(45) Date of Patent: Jul. 7, 2020

(54) BLEACHING AGENT WITH PERCARBONATES OR PERBORATES AND PERSULFATES

(71) Applicant: Henkel AG & Co. KGaA, Duesseldorf (DE)

(72) Inventors: Udo Erkens, Willich (DE); Torsten Lechner, Langenfeld (DE)

(73) Assignee: Henkel AG & Co. KGaA, Dusseldorf (DE)

( * ) Notice: Subject to any disclaimer, the term of this patent is extended or adjusted under 35 U.S.C. 154(b) by 0 days.

(21) Appl. No.: 16/212,434

(22) Filed: Dec. 6, 2018

(65) Prior Publication Data

US 2019/0175463 A1   Jun. 13, 2019

(30) Foreign Application Priority Data

Dec. 7, 2017  (DE) .................. 10 2017 222 125

(51) Int. Cl.

| | |
|---|---|
| *A61Q 5/08* | (2006.01) |
| *A61K 8/23* | (2006.01) |
| *A61Q 5/10* | (2006.01) |
| *A61K 8/44* | (2006.01) |
| *A61K 8/81* | (2006.01) |
| *A61K 8/22* | (2006.01) |
| *A61K 8/24* | (2006.01) |
| *A61K 8/19* | (2006.01) |
| *A61K 8/25* | (2006.01) |
| *A61K 8/73* | (2006.01) |
| *A45D 19/00* | (2006.01) |

(52) U.S. Cl.
CPC .................. *A61K 8/23* (2013.01); *A61K 8/19* (2013.01); *A61K 8/22* (2013.01); *A61K 8/24* (2013.01); *A61K 8/25* (2013.01); *A61K 8/44* (2013.01); *A61K 8/731* (2013.01); *A61K 8/8147* (2013.01); *A61K 8/8152* (2013.01); *A61Q 5/08* (2013.01); *A61Q 5/10* (2013.01); *A45D 2019/0066* (2013.01)

(58) Field of Classification Search
None
See application file for complete search history.

(56) References Cited

U.S. PATENT DOCUMENTS

| | | |
|---|---|---|
| 6,274,125 B1 | 8/2001 | Millequant et al. |
| 2011/0232669 A1* | 9/2011 | Suenger .................. A61K 8/44 132/208 |
| 2014/0326270 A1 | 11/2014 | Degeorge et al. |
| 2016/0235634 A1* | 8/2016 | Sato ....................... A61K 8/731 |
| 2018/0133127 A1 | 5/2018 | Anderheggen |

FOREIGN PATENT DOCUMENTS

| | | |
|---|---|---|
| DE | 19756454 C1 | 6/1999 |
| GB | 2556962 A | 6/2018 |
| GB | 2558339 A | 7/2018 |
| GB | 2560061 A | 8/2018 |
| WO | 9416672 A1 | 8/1994 |
| WO | 2016188773 A1 | 12/2016 |

\* cited by examiner

*Primary Examiner* — Jyothsna A Venkat
(74) *Attorney, Agent, or Firm* — Lorenz & Kopf, LLP

(57) ABSTRACT

The present disclosure relates to an agent for the oxidative changing of the colour of keratin fibres, containing—in relation to its total weight—
(a) one or more percompounds from the group of sodium percarbonate, potassium percarbonate, sodium perborate and potassium perborate in a total amount of from about 0.5 to about 14.0% by weight, and
(b) one or more persulfates from the group of ammonium persulfate, potassium persulfate, and sodium persulfate in a total amount of from about 5.0 to about 60.0% by weight, and
(c) less than about 10.0% by weight water.

2 Claims, No Drawings

BLEACHING AGENT WITH PERCARBONATES OR PERBORATES AND PERSULFATES

CROSS-REFERENCE TO RELATED APPLICATION

This application claims priority to German Patent Application No. 10 2017 222 125.9, filed Dec. 7, 2017, which is incorporated herein by reference in its entirety.

TECHNICAL FIELD

The present disclosure lies in the field of cosmetics and relates to agents for changing the colour oxidatively of keratin fibres, which agents contain percarbonates or perborates, persulfates and water, in each case in certain amount ranges. The present disclosure also relates to methods for changing the colour oxidatively of keratin fibres in which the aforementioned agents are used.

BACKGROUND

The changing of colour oxidatively, in particular the bleaching or lightening of the natural hair colour is traditionally the desire of many consumers, since a blonde hair colour is considered to be attractive and desirable from a fashion viewpoint. For this purpose, various bleaching agents with different bleaching power are obtainable on the market. The oxidants contained in these products are able to lighten the hair fibres due to the oxidative destruction of the hair's own pigment melanin and/or artificial dyes. For a moderate bleaching effect, the use of hydrogen peroxide—optionally with use of ammonia or other alkalising agents—as sole oxidant is sufficient, however a mixture of hydrogen peroxide and peroxo salts, in particular persulfate salts, is usually used in order to attain a stronger bleaching effect.

These peroxo salts are usually used in the form of a powder that is mixed with a hydrogen peroxide preparation just before application. The use of the combination of hydrogen peroxide and persulfates is associated with various disadvantages. The application of hydrogen peroxide to the scalp may lead to irritation. Also, at least two separately packaged components (the persulfate powder and the hydrogen peroxide solution) have to be mixed with one another in order to produce the ready-to-use bleaching agent. Users, who where possible support sustainable consumerism, are also paying increased attention to the ecological aspects of a product. One objective here is also a reduction of packaging material. Products that are used in the most concentrated form possible, which include merely one component and which in order to produce the application mixture in an optimal manner have to be mixed merely with water offer a key advantage in respect of the saving of packaging material.

In addition, the lightening known from the prior art is also associated with hair damage, since not only the pigments of the hair but also the other structural constituents of the hair are oxidatively damaged. Depending on the extent of the degree of damage, this ranges from coarse, brittle hair that is difficult to comb to a reduced resistance and tensile strength of the hair, as well as splitting through to hair breakage. The longer is the reaction time and the greater is the amount of used hydrogen peroxide and peroxodisulfates, generally the more severe is the damage caused to the keratin fibres. The discovery of new bleaching agents with reduced hair damage is therefore likewise an ever-existing challenge.

BRIEF SUMMARY

Agents and methods for the oxidative changing of the colour of keratin fibres are provided herein. In an embodiment, an agent for the oxidative changing of the colour of keratin fibres includes—in relation to its total weight—
(a) one or more percompounds from the group of sodium percarbonate, potassium percarbonate, sodium perborate and potassium perborate in a total amount of from about 0.5 to about 14.0% by weight,
(b) one or more persulfates from the group of ammonium persulfate, potassium persulfate, and sodium persulfate in a total amount of from about 5.0 to about 60.0% by weight, and
(c) less than about 10.0% by weight water.

In another embodiment, an agent for the oxidative changing of the colour of keratin fibres includes—in relation to its total weight—
(a) one or more percompounds from the group of sodium percarbonate, potassium percarbonate, sodium perborate and potassium perborate in a total amount of from about 0.5 to about 14.0% by weight, wherein the agent comprises from about 6.0 to 10.0% by weight of sodium percarbonate, and
(b) one or more persulfates from the group of ammonium persulfate, potassium persulfate, and sodium persulfate, wherein the agent comprises from about 9.0 to about 14.0% by weight of ammonium persulfate, from about 27.0 to about 42.0% by weight of potassium persulfate, and from about 1.5 to about 4.0% by weight of sodium persulfate,
(c) less than about 10.0% by weight water,
one or more alkalising agents chosen from the group of alkaline (earth) metal silicates, alkaline (earth) metal metasilicates, alkaline (earth) metal hydroxides, alkaline (earth) metal phosphates, alkaline (earth) metal hydrogen phosphates, alkaline (earth) metal carbonates and basic amino acids, and
one or more anionic polymers chosen from the group of (co)polymers of methacrylic acid and (co)polymers of acrylic acid in a total amount of from about 0.75 to about 1.5% by weight.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

The object of the present disclosure is therefore to provide agents for the oxidative changing of colour which enable a bleaching of the keratin fibres without the use of hydrogen peroxide solutions. These agents should include merely one component, and it should be possible to produce the ready-to-use agent by mixing with water. In addition, these agents should damage the hair to a minimal extent but with maximum lightening power.

Bleaching agents that include a powdery component and that form the ready-to-use agent when mixed with water are known for example from WO 94/16672 A1. In this document percarbonates (in particular sodium percarbonate) is used as solid hydrogen peroxide source and is used mixed with persulfates in order to bleach the hair.

WO 94/16672 A1 teaches that the substances releasing the hydrogen peroxide (i.e. in particular the percarbonates) have to be used in very high amounts of from 15 to 23% by weight (in relation to the total weight of the agent). When reworking the teaching of WO 94/16672 A1, however, it was found that these high use amounts of percarbonates lead to very severe hair damage that is no longer acceptable to the user. Thus, it was sought to find ways to minimise the hair damage of these agents without also reducing their bleaching power.

It has been found that the hair damage could be reduced if smaller amounts of percarbonates or perborates were used in the agents. Here, it was surprising that—provided the optimal content of percarbonates (or perborates) was selected and the percarbonates (or perborates) were used in specified ratios in comparison to the persulfates—this reduction of hair damage was possible with full retention of the bleaching power.

A first subject of the present disclosure is an agent for the oxidative changing of the colour of keratin fibres, containing—in relation to its total weight—
(a) one or more percompounds from the group of sodium percarbonate, potassium percarbonate, sodium perborate and potassium perborate in a total amount of from about 0.5 to about 14.0% by weight, and
(b) one or more persulfates from the group of ammonium persulfate, potassium persulfate, and sodium persulfate in a total amount of from about 5.0 to about 60.0% by weight, and
(c) less than about 10.0% by weight water.

Agent for the Oxidative Changing of the Colour of Keratin Fibres

The agents as contemplated herein are used for the oxidative changing of the colour of keratin fibres. The term "oxidative changing of the colour" used as contemplated herein shall be understood to mean bleaching agents and also agents for lightening keratin fibres which contain the oxidants of groups (a) and (b) (percarbonates/perborates and persulfates). If pure bleaching or lightening is sought, the agents do not contain any further dyes. However, it can also be desirable to change the colour shade of the keratin fibres in addition to the bleaching/lightening. For the purpose of changing the colour shade, the agents as contemplated herein can additionally also contain colouring components, such as substantive dyes and/or oxidation dye precursor products. The preferred purpose of the agents, however, is bleaching or lightening, and therefore the agents preferably contain either no dyes or contain these only in small amounts suitable for a minor colour shade change.

Keratin fibres are understood to mean wool, furs, feathers and in particular human hair. The dyes as contemplated herein, however, can also be used in principle to dye other natural fibres, such as cotton, jute, sisal, linen or silk, modified natural fibres, such as regenerated cellulose, nitro, alkyl or hydroxyalkyl or acetyl cellulose.

Percarbonates and Perborates

As first constituent (a) essential to the present disclosure the agents as contemplated herein contain—in relation to their total weight—one or more percompounds from the group of sodium percarbonate, potassium carbonate, sodium perborate and potassium perborate in a total amount of from about 0.5 to about 14.0% by weight.

In the sense of the present disclosure sodium percarbonate is understood to mean the adduct (or the complex) of sodium carbonate and hydrogen peroxide with the composition 2 $Na_2CO_3 \times 3\ H_2O_2$. Sodium percarbonate forms a white, water-soluble powder that is broken down formally into sodium carbonate and hydrogen peroxide upon contact with water. The sodium percarbonate as contemplated herein (2 $Na_2CO_3 \times 3\ H_2O_2$) has a molar mass of 314.02 g/mol and has the CAS number 15630-89-4.

Sodium percarbonate is commercially obtainable from various providers in different degrees of purity. For example, the company Evonik Degussa offers a sodium percarbonate with a purity of about 98.8% by weight. All of the aforementioned amount values relate to 100% sodium percarbonate. With use of sodium percarbonate in lower degrees of purity, the usage amounts must be recalculated accordingly. Similarly, in the sense of the present disclosure, potassium percarbonate is understood to mean the adduct (or the complex) of potassium carbonate and hydrogen peroxide with the composition 2 $K_2CO_3 \times 3\ H_2O_2$.

Sodium perborate is alternatively also referred to as sodium peroxoborate. Sodium perborate as contemplated herein is the commercially available sodium peroxoborate tetrahydrate (sodium perborate tetrahydrate) with the molecular formula ($NaBO_3.4H_2O$). Alternatively, the literature also contains the molecular formula $NaBO_2.H_2O_2.3H_2O$. In the solid state, ring-shaped peroxoborates are present, with the formula $Na_2B_2(O_2)_2(OH)_4.6H_2O$. Sodium perborate tetrahydrate has the CAS no. 10486-00-7 and is sold commercially for example by the company Sigma Aldrich.

The use of sodium percarbonate has proven to be particularly well suited for solving the problem stated as contemplated herein.

What is particularly preferred is an agent for the oxidative changing of the colour of keratin fibres, containing—in relation to its total weight—
(a) from about 0.5 to about 14.0% by weight of sodium percarbonate and
(b) one or more persulfates from the group of ammonium persulfate, potassium persulfate, and sodium persulfate in a total amount of from about 5.0 to about 60.0% by weight, and
(c) less than about 10.0% by weight water.

The agents as contemplated herein contain the percarbonates and the perborates in a total amount of from about 0.5 to about 14.0% by weight.

The works leading to this present disclosure have shown that a further increase of the percarbonate and perborate amount beyond about 14.0% by weight indeed increases hair damage, but does not lead to a further increase in the lightening. In this context it has proven to be particularly preferred to use one or more percarbonates in the agents as contemplated herein in a total amount of from about 1.5 to about 13.0% by weight, preferably from about 3.0 to about 12.0% by weight, more preferably from about 4.5 to about 11.0% by weight, and very particularly preferably from about 6.0 to about 10.0% by weight. The best lightening power with comparatively minimal hair damage could be obtained if the agents contained the percarbonates (in particular sodium percarbonate) in a total amount of from about 6.0 to about 10.0% by weight.

All values in % by weight relate here to the total amount of the percarbonates (sodium percarbonate and/or potassium percarbonate) used in the agent and perborates (sodium perborate and/or potassium perborate), which is set in relation to the total weight of the agent.

In a particularly preferred embodiment an agent as contemplated herein contains—in relation to its total weight—
(a) one or more percarbonates from the group of sodium percarbonate and potassium percarbonate in a total amount of from about 1.5 to about 13.0% by weight, preferably from about 3.0 to about 12.0% by weight, more preferably from about 4.5 to about 11.0% by weight, and very particularly preferably from about 6.0 to about 10.0% by weight.

In a very particularly preferred embodiment an agent as contemplated herein contains—in relation to its total weight—
(a) from about 0.5 to about 14.0% by weight, preferably from about 1.5 to about 13.0% by weight, more preferably from about 3.0 to about 12.0% by weight, even more preferably from about 4.5 to about 11.0% by weight, and very particularly preferably from about 6.0 to about 10.0% by weight of sodium percarbonate.

Persulfates

As second constituent (b) essential to the present disclosure the agents as contemplated herein contain one or more persulfates from the group of ammonium persulfate, potassium persulfate and sodium persulfate in a total amount of from about 5.0 to about 60.0% by weight.

Ammonium persulfate is alternatively also referred to as ammonium peroxodisulfate and has the molecular formula $(NH_4)_2S_2O_8$. Ammonium persulfate has the CAS number 7727-54-0.

Potassium persulfate is alternatively also referred to as potassium peroxodisulfate and has the molecular formula $K_2S_2O_8$. Potassium persulfate has the CAS number 7727-21-1.

Sodium persulfate is alternatively also referred to as sodium peroxodisulfate and has the molecular formula $Na_2S_2O_8$. Sodium persulfate has the CAS number 7775-27-1.

The persulfates are also preferably used in certain total amounts in the agent as contemplated herein so as to both optimise the lightening power and minimise the hair damage.

In a very particularly preferred embodiment an agent as contemplated herein contains—in relation to its total weight—
(b) one or more persulfates from the group of ammonium persulfate, potassium persulfate and sodium persulfate in a total amount of from about 10.0 to about 55.0% by weight, preferably from about 15.0 to about 50.0% by weight, more preferably from about 20.0 to about 48.0% by weight, and very particularly preferably from about 30.0 to about 45.0% by weight.

It has also proven to be advantageous if the agents contain at least two persulfates from the group of ammonium persulfate, sodium persulfate and potassium persulfate. It is very particularly preferred if the agents as contemplated herein contain all three persulfates—ammonium persulfate, sodium persulfate and potassium persulfate.

It is particularly preferred if the agent as contemplated herein contains from about 3.0 to about 20.0% by weight, preferably from about 5.0 to about 18.0% by weight, more preferably from about 7.0 to about 16.0% by weight, and very particularly preferably from about 9.0 to about 14.0% by weight of ammonium persulfate.

In a very particularly preferred embodiment an agent as contemplated herein contains—in relation to its total weight—
(b) from about 3.0 to about 20.0% by weight, preferably from about 5.0 to about 18.0% by weight, more preferably from about 7.0 to about 16.0% by weight, and very particularly preferably from about 9.0 to about 14.0% by weight of ammonium persulfate.

It is particularly preferred if the agent as contemplated herein contains from about 15.0 to about 50.0% by weight, preferably from about 18.0 to about 47.0% by weight, more preferably from about 20.0 to about 45.0% by weight, and very particularly preferably from about 27.0 to about 42.0% by weight of potassium persulfate.

In a very particularly preferred embodiment an agent as contemplated herein contains—in relation to its total weight—
(b) from about 15.0 to about 50.0% by weight, preferably from about 18.0 to about 47.0% by weight, more preferably from about 20.0 to about 45.0% by weight, and very particularly preferably from about 27.0 to about 42.0% by weight of potassium persulfate.

It is particularly preferred if the agent as contemplated herein contains from about 0.1 to about 10.0% by weight, preferably from about 0.5 to about 8.0% by weight, more preferably from about 1.0 to about 6.0% by weight, and very particularly preferably from about 1.5 to about 4.0% by weight of sodium persulfate.

In a very particularly preferred embodiment an agent as contemplated herein contains—in relation to its total weight—
(b) from about 0.1 to about 10.0% by weight, preferably from about 0.5 to about 8.0% by weight, more preferably from about 1.0 to about 6.0% by weight, and very particularly preferably from about 1.5 to about 4.0% by weight of sodium persulfate.

What is particularly preferred is an agent for the oxidative changing of the colour of keratin fibres, containing—in relation to its total weight—
(a) from about 0.5 to about 14.0% by weight of sodium percarbonate and
(b1) from about 3.0 to about 20.0% by weight of ammonium persulfate and
(b2) from about 15.0 to about 50.0% by weight of potassium persulfate and
(b3) from about 0.1 to about 10.0% by weight of sodium persulfate and
(c) less than about 10.0% by weight water.

What is particularly preferred is an agent for the oxidative changing of the colour of keratin fibres, containing—in relation to its total weight—
(a) from about 1.5 to about 13.0% by weight of sodium percarbonate and
(b1) from about 3.0 to about 20.0% by weight of ammonium persulfate and
(b2) from about 15.0 to about 50.0% by weight of potassium persulfate and
(b3) from about 0.1 to about 10.0% by weight of sodium persulfate and
(c) less than about 10.0% by weight water.

What is particularly preferred is an agent for the oxidative changing of the colour of keratin fibres, containing—in relation to its total weight—
(a) from about 3.0 to about 12.0% by weight of sodium percarbonate and
(b1) from about 5.0 to about 18.0% by weight of ammonium persulfate and
(b2) from about 18.0 to about 47.0% by weight of potassium persulfate and
(b3) from about 0.5 to about 8.0% by weight of sodium persulfate and
(c) less than about 10.0% by weight water.

What is particularly preferred is an agent for the oxidative changing of the colour of keratin fibres, containing—in relation to its total weight—
(a) from about 4.5 to about 11.0% by weight of sodium percarbonate and (b1) from about 7.0 to about 16.0% by weight of ammonium persulfate and
(b2) from about 20.0 to about 45.0% by weight of potassium persulfate and
(b3) from about 1.0 to about 6.0% by weight of sodium persulfate and
(c) less than about 10.0% by weight water.

What is particularly preferred is an agent for the oxidative changing of the colour of keratin fibres, containing—in relation to its total weight—
(a) from about 6.0 to about 10.0% by weight of sodium percarbonate and
(b1) from about 9.0 to about 14.0% by weight of ammonium persulfate and
(b2) from about 24.0 to about 42.0% by weight of potassium persulfate and
(b3) from about 1.5 to about 4.0% by weight of sodium persulfate and
(c) less than about 10.0% by weight water.

Water Content of the Agent

The agents as contemplated herein are present in the form of a single component that has to be mixed merely with water in order to produce the ready-to-use agent. The mixing with a second, separately packaged preparation can be spared in this way, and packaging material and the associated costs can be saved. When mixing with water, hydrogen peroxide (or "active oxygen") is released from the percarbonates (or perborates) in situ. Since the contact with water converts the agent into its ready-to-use form, the agent itself is substantially anhydrous and thus contains less than about 10.0% by weight water (c). For example, 100 g of an agent as contemplated herein contain at most 9.9% by weight (=9.9 g) water.

Various raw materials can contain small amounts of water, for example if the raw materials are used in the form of an emulsion, contain water of crystallisation, or water is present as a minor component. With use of these raw materials, smaller amounts of water can thus be introduced into the agents as contemplated herein. It is particularly advantageous, however, to choose the water content to be as low as possible.

What is particularly preferred is an agent for the oxidative changing of the colour of keratin fibres containing—in relation to its total weight—(c) less than about 5.0% by weight water, more preferably less than about 2.5% by weight water, even more preferably less than about 1.0% by weight water, and very particularly preferably less than about 0.1% by weight water.

In a very particularly preferred embodiment an agent as contemplated herein contains—in relation to its total weight—
(c) less than about 5.0% by weight, preferably less than about 2.5% by weight, more preferably less than about 1.0% by weight, and very particularly preferably less than about 0.1% by weight water.

A very easily handled formulation, which has a low water content or is anhydrous, that is comfortable for the user is constituted by providing the agent in the form of a powder or a paste. The agent is therefore very particularly preferably present in the form of a powder (such as a bleaching powder) or in the form of a paste (such as a bleaching paste).

In a particularly preferred embodiment an agent as contemplated herein is present in the form of a powder or in the form of a paste.

In a particularly preferred embodiment an agent as contemplated herein is present in the form of a bleaching powder or in the form of a bleaching paste.

In a very particularly preferred embodiment an agent as contemplated herein is present in the form of a bleaching powder.

In other words, the agents as contemplated herein in a particularly preferred embodiment is a bleaching powder or a bleaching paste containing—in each case in relation to the total weight of the powder or the paste—
(a) one or more percarbonates from the group of sodium percarbonate and potassium percarbonate in a total amount of from about 0.5 to about 14.0% by weight, and
(b) one or more persulfates from the group of ammonium persulfate, potassium persulfate, and sodium persulfate in a total amount of from about 5.0 to about 60.0% by weight, and
(c) less than about 10.0% by weight water.

In other words, the agent as contemplated herein in a very particularly preferred embodiment is a bleaching powder containing—in each case in relation to the total weight of the powder—
(a) one or more percarbonates from the group of sodium percarbonate and potassium percarbonate in a total amount of from about 0.5 to about 14.0% by weight, and
(b) one or more persulfates from the group of ammonium persulfate, potassium persulfate, and sodium persulfate in a total amount of from about 5.0 to about 60.0% by weight, and
(c) less than about 10.0% by weight water.

In other words, the agent as contemplated herein in a very particularly preferred embodiment is a bleaching powder containing—in each case in relation to the total weight of the powder—
(a) from about 0.5 to about 14.0% by weight of sodium percarbonate and
(b) one or more persulfates from the group of ammonium persulfate, potassium persulfate, and sodium persulfate in a total amount of from about 5.0 to about 60.0% by weight, and
(c) less than about 10.0% by weight water.

The terms "powder" or "powdery" within the scope of the present disclosure shall be understood to mean agents that include comminuted, solid constituents, wherein the comminution can be attained by crushing, pounding, grinding or by spray drying or freeze drying. A powder is thus a mixture of small, solid particles. Powders can be composed of solid constituents having different particle sizes. It can usually be preferred, however, if the powders have the most homogeneous particle size possible, in particular so as to facilitate a uniform dispersion or dissolution of the powders in water. A preferred powder in the sense of the present disclosure has a mean particle diameter of at least about 20 µm and a BET surface of from about 40 to about 400 m$^2$/g.

The terms "paste" or "pasty" as contemplated herein shall be understood to mean an administration form that has a viscosity at 20° C. and 1013 mbar in the range of from about 200,000 to about 1,600,000 mPas, preferably from about 250,000 to about 1,400,000 mPas, particularly preferably from about 300,000 to about 1,000,000 mPas, extremely preferably from about 400,000 to about 750,000 mPas The paste viscosity is preferably determined by employing Brookfield; apparatus RVDV II+; spindle no. 96, 4 revolutions per minute, at 20° C. Unless specified otherwise, all temperature values relate to a pressure of 1013 mbar.

Amount Specifications

As described previously, the agents as contemplated herein are exemplified in that they contain constituents (a) and (b) in each case in specific amount ranges. The constituent (c) (water) is provided in the agent at most in the specified maximum amount. Here, all specified amounts add up to at most 100% by weight.

The minimum amounts of the constituents of groups (a) contained in the agent lie at about 0.5% by weight, and the minimum amount of the constituents from group (b) contained in the agent lies at about 5.0% by weight. In this case the agent also contains a large proportion of other ingredients. For example, the agents as contemplated herein—depending on the level at which the content of (a) and (b) is selected—can additionally contain fillers, surfactants, fatty substances, oils, nourishing agents, etc. in different value ranges. The additional optional constituents are described in the following portions.

Alkalising Agent

The agent as contemplated herein is preferably of such a composition that the ready-to-use agent obtained by mixing with water has an alkali pH value. The ready-to-use agent preferably has a pH value of from about 8 to about 11.5, particularly preferably a pH value of from about 8.5 to about 11, extremely preferably a pH value of from about 9.0 to about 10.5, in each case measured at 20° C.

Percarbonates, in particular sodium percarbonate, dissolve in water and form an alkaline pH value. Depending on the total amount of the percarbonates used in the agent, the alkaline pH value in the ready-to-use agent can therefore be set already by the percarbonates alone.

In particular if the percarbonates are used in smaller amounts or if the ready-to-use agent should have a particularly alkaline pH value, it may be advantageous to additionally incorporate a further alkalising agent into the agent. Since the agents are preferably formulated as a powder or a paste, particularly well-suited alkalising agents are solid at room temperature (20° C.).

The alkalising agents usable as contemplated herein are preferably selected from alkaline (earth) metal metasilicates, alkaline (earth) metal metasilicates, alkaline (earth) metal hydroxides, alkaline (earth) metal phosphates, alkaline (earth) metal hydrogen phosphates, and basic amino acids. Lithium, sodium and/or potassium are preferably used as alkaline metal ions. Magnesium and/or calcium are preferably used as alkaline earth metal ions.

Particularly well suited basic amino acids are arginine, histidine and lysine and/or salts thereof. Salts of arginine, lysine and histidine that are preferably suitable as contemplated herein include the ammonium salts, alkaline metal salts, and alkaline earth metal salts, in particular the lithium, sodium, potassium, magnesium and calcium salts, and in addition the hydrogen halides, in particular the hydrochlorides, and mixtures of these salts. An amino acid salt that is particularly preferred as contemplated herein is lysine hydrochloride. The amino acids that are suitable as contemplated herein, selected from arginine, lysine, histidine and salts thereof, can also contain water of crystallisation.

In a particularly preferred embodiment an agent as contemplated herein contains one or more alkalising agents from the group of alkaline (earth) metal silicates, alkaline (earth) metal metasilicates, alkaline (earth) metal hydroxides, alkaline (earth) metal phosphates, and alkaline (earth) metal hydrogen phosphates, alkaline (earth) metal carbonates and basic amino acids.

The usage amounts of the alkalising agent(s) are selected by a person skilled in the art depending on the pH value that should be set in the ready-to-use agent.

The agent—in relation to its total weight—may thus contain one or more alkalising agents from the group of alkaline (earth) metal silicates, alkaline (earth) metal metasilicates, alkaline (earth) metal hydroxides, alkaline (earth) metal phosphates, and alkaline (earth) metal hydrogen phosphates and basic amino acids in a total amount of from about 5.0 to about 60.0% by weight, preferably from about 10.0 to about 55.0% by weight, more preferably from about 15.0 to about 50.0% by weight, and very particularly preferably from about 20.0 to about 45.0% by weight.

Further Constituents

The agents as contemplated herein may additionally also contain further constituents. The agents—in particular if they are to be formulated as pastes—may thus additionally contain at least one oil. Preferred oils can be selected from paraffin oil, silicone oil, or ester oil and mixtures of these oils.

Further oils that are preferred as contemplated herein are selected from natural and synthetic hydrocarbons, particularly preferably from paraffin oils, $C_{18}$-$C_{30}$ isoparaffins, in particular isoeicosan, polyisobutenes and polydecenes, furthermore selected from $C_8$-$C_{16}$ isoparaffins, in particular from isodecane, isododecane, isotetradecane and isohexadecane and mixtures hereof, and 1,3-di-(2-ethylhexyl)-cyclohexane.

Further oils that are preferred as contemplated herein are selected from the benzoic acid esters of linear or branched C8-22 alkanols. Benzoic acid C12-C15 alkyl esters are particularly preferred.

Further oils that are preferred as contemplated herein are selected from fatty alcohols with from about 6 to about 30 carbon atoms that are unsaturated or branched and saturated or branched and unsaturated. Preferred alcohol oils are 2-hexyldecanol, 2-octyldodecanol, 2-ethylhexyl alcohol and isostearyl alcohol and mixtures hereof.

Further cosmetic oils that are preferred as contemplated herein are selected from the triglycerides (—triple esters of glycerol) of linear or branched, saturated or unsaturated, optionally hydroxylated $C_{8-30}$ fatty acids. The use of natural oils, for example amaranth seed oil, apricot kernel oil, argan oil, avocado oil, babassu oil, cottonseed oil, borage seed oil, camelina oil, thistle oil, peanut oil, pomegranate seed oil, grapefruit seed oil, hemp oil, hazelnut oil, elderberry seed oil, blackcurrant seed oil, jojoba oil, linseed oil, macadamia nut oil, corn oil, almond oil, marula oil, evening primrose oil, olive oil, palm oil, palm kernel oil, para nut oil, pecan nut oil, peach kernel oil, rapeseed oil, castor oil, sea buckthorn pulp oil, sea buckthorn seed oil, sesame oil, soy oil, sunflower oil, grapeseed oil, walnut oil, wild rose oil, wheat germ oil, and the liquid components of coconut oil and the like, can be particularly preferred. Synthetic triglyceride oils are also preferred, however, in particular capric/caprylic triglycerides.

Further cosmetic oils that are particularly preferred as contemplated herein are selected from the dicarboxylic acid esters of linear or branched $C_2$-$C_{10}$ alkanols, in particular diisopropyl adipate, di-n-butyl adipate, di-(2-ethylhexyl) adipate, dioctyl adipate, diethyl/di-n-butyl/dioctyl sebacate, diisopropyl sebacate, dioctyl malate, dioctyl maleate, dicaprylyl maleate, diisooctyl succinate, di-2-ethylhexyl succinate, and di-(2-hexyldecyl)succinate.

Further cosmetic oils that are particularly preferred as contemplated herein are selected from esters of linear or branched, saturated or unsaturated fatty alcohols having from about 2 to about 30 carbon atoms with linear or branched, saturated or unsaturated fatty acids having from about 2 to about 30 carbon atoms, which can be hydroxylated. These preferably include 2-hexyldecyl stearate, 2-hexyldecyl laurate, isodecyl neopentanoate, isononyl isononanoate, 2-ethylhexyl palmitate, and 2-ethylhexyl stearate, isopropyl myristate, isopropyl palmitate, isopropyl stearate, isopropyl isostearate, isopropyl oleate, isooctyl stearate, isononyl stearate, isocetyl stearate, isononyl isononanoate, isotridecyl isononanoate, cetearyl isononanoate, 2-ethylhexyl laurate, 2-ethylhexyl isostearate, 2-ethylhexyl cocoate, 2-octyldodecyl palmitate, butyl octanoic acid-2-butyl octanoate, diisotridecyl acetate, n-butyl stearate, n-hexyl laurate, n-decyl oleate, oleyl oleate, oleyl erucate, erucyl oleate, erucyl erucate and ethylene glycol dioleate.

Further cosmetic oils that are preferred as contemplated herein are selected from the addition products of from about 1 to about 5 propylene oxide units with mono- or polyvalent $C_{8-22}$ alkanols such as octanol, decanol, decanediol, lauryl alcohol, myristyl alcohol, and stearyl alcohol, e.g. PPG-2 Myristyl Ether and PPG-3 Myristyl Ether. Further cosmetic oils that are preferred as contemplated herein are selected from addition products of at least about 6 ethylene oxide and/or propylene oxide units with mono- or polyvalent $C_{3-22}$ alkanols such as glycerol, butanol, butanediol, myristyl alcohol, and stearyl alcohol, which can be esterified if desired, e.g. PPG-14 Butyl Ether, PPG-9 Butyl Ether, PPG-10 Butanediol, PPG-15 Stearyl Ether, and Glycereth-7 diisononaoate.

Further cosmetic oils that are preferred as contemplated herein are selected from $C_8$-$C_{22}$ fatty alcohol esters of monovalent or polyvalent $C_2$-$C_7$ hydroxycarboxylic acids, in particular the esters of glycolic acid, lactic acid, malic acid, tartaric acid, citric acid, and salicylic acid, for example $C_{12}$-$C_{15}$ alkyl lactate.

Further cosmetic oils that are preferred as contemplated herein are selected from symmetrical, asymmetrical, or cyclic esters of carbonic acid with $C_{3-22}$ alkanols, $C_{3-22}$ alkanediols, or $C_{3-22}$ alkanetriols, e.g. dicaprylyl carbonate, or the esters according to DE 19756454 A1, in particular glycerol carbonate.

Further cosmetic oils that are suitable in accordance with the present disclosure are selected from the silicone oils that include, for example, dialkyl and alkylaryl siloxanes, for example decamethylcyclopentasiloxane, dodecamethylcyclohexasiloxane, dimethylpolysiloxane and methylphenylpolysiloxane, but also hexamethyldisiloxane, octamethyltrisiloxane and decamethyltetrasiloxane.

Mixtures of the aforementioned oils can be used extremely preferably as contemplated herein.

The agents as contemplated herein can furthermore contain one or more thickeners. Preferred thickeners are selected from copolymers of $C_2$-$C_4$ alkene and styrene, linear saturated 1-alkanols having from about 12 to about 30 carbon atoms, esters of saturated branched or unbranched alkane carboxylic acids having from about 12 to about 24 C atoms, and saturated branched or unbranched alcohols having from about 16 to about 50 C atoms, wherein the esters have a melting point in the range of from about 50° C. to about 110° C., triglycerides of saturated and optionally hydroxylated $C_{12-30}$ fatty acids, wherein the triglycerides have a melting point in the range of from about 50° C. to about 110° C., and mixtures of the aforementioned substances.

Copolymers of C2-C4 alkene and styrene that are preferred as contemplated herein are selected from copolymers of ethylene/propylene/styrene, copolymers of butylene/ethylene/styrene, copolymers of butylene/propylene/styrene and mixtures of these copolymers.

The aforementioned copolymers of C2-C4 alkene and styrene preferably are not copolymers in which the monomer units are randomly distributed, but instead block copolymers, particularly preferably diblock copolymers and triblock copolymers. Such block copolymers have "hard" segments formed of polystyrene and "soft" segments formed of ethylene/propylene or ethylene/butylene or propylene/butylene. The individual blocks can comprise, here, from about 10 to about 10000, preferably from about 50 to about 5000, and in particular from about 100 to about 500 monomers. Preferred diblock copolymers are styrene-ethylene propylene (S-EP) and styrene-ethylene butylene (S-EB); preferred triblock copolymers are styrene-ethylene propylene-styrene (S-EP-S) and styrene-ethylene butylene-styrene (S-EB-S). Mixtures of diblock and triblock copolymers are used with particular preference as contemplated herein, wherein mixtures of styrene-ethylene propylene (S-EP) and styrene-ethylene propylene-styrene (S-EP-S) have proven to be particularly preferred. Here, the proportion of diblock copolymers very particularly preferably contributes to from about 10 to about 90% by weight, and the proportion of triblock copolymers very particularly preferably contributes to from about 90 to about 10% by weight, in each case in relation to the weight of the polymer mixture.

Triglycerides in the sense of the present disclosure are triesters of glycerol, i.e. esters, in which all OH groups of the glycerol are esterified with acid, in the present case with a saturated and optionally hydroxylated $C_{12-30}$ fatty acid.

Triglycerides of saturated and optionally hydroxylated $C_{12-30}$ fatty acids having a melting point in the range of from about 50° C. to about 110° C. that are preferred as contemplated herein and that thicken the oil phase are selected from hardened triglyceride fats, in particular hydrogenated palm oil, hydrogenated coconut oil, hydrogenated castor oil, glyceryl tribehenate (tribehenin) or glyceryl tri-12-hydroxystearate, as well as mixtures thereof. Hydrogenated castor oil, obtainable for example as commercial product Cutina® HR, is particularly preferred as contemplated herein.

Agents that are particularly preferred as contemplated herein also contain at least one or more hydrophilic thickeners preferably selected from polysaccharides which can be chemically and/or physically modified, acrylic acid homo- and copolymers, methacrylic acid homo- and copolymers, itaconic acid homo- and copolymers, and mixtures of these polymers.

Hydrophilic thickeners that are suitable as contemplated herein include acrylic acid homo- and copolymers, methacrylic acid homo- and copolymers, itaconic acid homo- and copolymers, preferably selected from the group formed by the crosslinked and uncrosslinked homo- or copolymers of acrylic acid, methacrylic acid and salts thereof and alkyl esters, homo- or copolymers of acrylic acid amides and/or methacrylic acid amides, copolymers of acrylic acid and acrylic acid amides and mixtures thereof, copolymers of ethoxylated C1-C6 alkyl esters of methacrylic acid and the sulfonated acrylic acid amides and salts thereof and crosslinked copolymers of methacrylic acid, acrylic acid amides and the sulfonated acrylic acid amides and salts thereof. The above-mentioned polymers and copolymers can be crosslinked or uncrosslinked. Provided the above-mentioned polymers and copolymers do not have any alkyl groups with a chain length of at least about 8 carbon atoms, they are preferably crosslinked. Provided the above-mentioned polymers and copolymers have alkyl groups with a chain length of at least about 8 carbon atoms, they are preferably uncrosslinked.

Examples of polymers that are preferred as hydrophilic thickeners are those known for example under the INCI name Copolymer Ammonium Acryloyldimethyltaurate/Beheneth-25 methacrylate Crosspolymer (trade name: Aristoflex HMB; Clariant), the copolymers known under the INCI name Acrylates/C10-30 Alkyl Acrylate Crosspolymer, and the crosslinked copolymer known under the INCI name Polyacrylate Crosspolymer-11 (trade name: Aristoflex Velvet; Clariant).

In a further very particularly preferred embodiment an agent as contemplated herein contains one or more anionic polymers from the group of (co)polymers of methacrylic acid and (co)polymers of acrylic acid in a total amount of from about 0.1 to about 5.0% by weight, preferably from about 0.25 to about 2.5% by weight, more preferably from about 0.6 to about 2.0% by weight, and very particularly preferably from about 0.75 to about 1.5% by weight.

Compounds from the group of polysaccharides are in particular suitable as hydrophilic thickeners. Examples include representatives of the celluloses (cellulose itself and derivatives thereof), alginic acids (and their corresponding physiologically acceptable salts, the alginates), agar agar (with the polysaccharide agarose present as main constituent in agar agar), starch fractions and derivatives such as amylose, amylopectin and dextrins, karaya rubber, locust bean gum, gum arabic, dextrans, guar gum and xanthan gum.

Suitable cellulose derivatives are methyl celluloses, ethyl celluloses, hydroxyalkyl celluloses (such as hydroxyethyl cellulose), methylhydroxyalkyl celluloses, and carboxymethyl celluloses (such as those with the INCI name Cellulose Gum) and also their physiologically acceptable salts.

From the group of polysaccharides, anionic polysaccharides such as carboxymethyl celluloses, alginic acid and xanthan gum are preferably selected for the thickening of the agents as contemplated herein. Carboxymethyl celluloses, alginic acids and xanthan gum, in addition to their physiologically acceptable salts, are referred to within the scope of the present disclosure as anionic polysaccharides, since the carboxylic acid groups present in these polysaccharides necessarily dissociate to a greater or lesser extent in water or aqueous formulation, whereby anionic carboxylate groups are formed, of which the number increases further with rising pH value. In preferred embodiments, carboxymethyl cellulose (preferably carboxymethyl cellulose with the INCI name Cellulose Gum) is contained as hydrophilic thickener in view of a reliable viscosity adjustment and residue-free application to keratin fibres and the scalp. Carboxymethyl cellulose can be contained in a preferred embodiment as the sole hydrophilic thickener. However, in particular a combination of carboxymethyl cellulose and xanthan (preferably xanthan with the INCI name Xanthan Gum) or physiologically acceptable salts thereof is also preferred. The physiologically acceptable salts are understood to mean in particular the sodium salts, but also the potassium salts, and also magnesium and calcium salts.

In a further very particularly preferred embodiment an agent as contemplated herein contains—in relation to its total weight—one or more anionic polysaccharides from the group of carboxymethyl cellulose, xanthan (xanthan gum), alginate (algin) and the physiologically acceptable salts thereof in a total amount of from about 0.1 to about 10.0% by weight, preferably from about 0.5 to about 8.0% by weight, more preferably from about 0.7 to about 6.0% by weight, and very particularly preferably from about 1.0 to about 5.0% by weight.

The agents as contemplated herein can furthermore also contain anionic, non-ionic and cationic zwitterionic and amphoteric surfactants.

All anionic surface-active substances suitable for use on the human body are suitable as anionic surfactants in the compositions as contemplated herein. These are exemplified by a water-soluble-making anionic group, such as a carboxylate, sulfate, sulfonate or phosphate group and a lipophilic alkyl group having from about 8 to about 30 C atoms. In addition, glycol or polyglycolether groups, ester, ether and amide groups and also hydroxyl groups can be contained in the molecule. Examples of suitable anionic surfactants are linear and branched fatty acids having from about 8 to about 30 C atoms (soaps), alkylether carboxylic acids, acyl sarcosides, acyl taurides, acyl isethionates, sulfosuccinic acid monoesters and dialkylesters and sulfosuccinic acid mono-alkylpolyoxyethyl esters, linear alkane sulfonates, linear alpha-olefin sulfonates, alkylsulfates and alkylether sulfates and also alkyl and/or alkenyl phosphates. Preferred anionic surfactants are alkyl sulfates, alkylether sulfates and alkylether carboxylic acids each having from about 10 to about 18 C atoms, preferably from about 12 to about 14 C atoms in the alkyl group and up to about 12 glycolether groups, preferably from about 2 to about 6 glycol ether groups in the molecule. Examples of such surfactants are the compounds with the INCI names Sodium Laureth Sulfate, Sodium Lauryl Sulfate, Sodium Myreth Sulfate or Sodium Laureth Carboxylate.

Surface-active compounds that carry, in the molecule, at least one quaternary ammonium group and at least one carboxylate, sulfonate or sulfate group are referred to as zwitterionic surfactants. Particularly suitable zwitterionic surfactants are what are known as betaines, such as the N-alkyl-N,N-dimethylammonium glycinates, for example coco-alkyl-dimethylammonium glycinate, N-acyl-aminopropyl-N,N-dimethylammonium glycinates, for example coco-acylaminopropyl-dimethylammonium glycinate, and 2-alkyl-3-carboxymethyl-3-hydroxyethyl imidazoline each having from about 8 to about 18 C atoms in the alkyl or acyl group and also coco-acylaminoethylhydroxyethylcarboxymethyl glycinate. A preferred zwitterionic surfactant is the fatty acid amide derivative known under the INCI name Cocamidopropyl Betaine.

Amphoteric surfactants are understood to be surface-active compounds which, in addition to a $C_8$-$C_{24}$ alkyl or acyl group, also contain at least one free amino group and at least one —COOH— or —SO$_3$H group in the molecule and are capable of forming inner salts. Examples of suitable amphoteric surfactants are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkyl aminopropionic acids, and alkyl amino acetic acids each having from about 8 to about 24 C atoms in the alkyl group. Particularly preferred amphoteric surfactants are N-coco-alkylaminopropionate, coco-acylaminoethylaminopropionate, and $C_{12}$-$C_{18}$ acyl sarcosine.

Non-ionic surfactants contain, as hydrophilic group, for example a polyol group, a polyalkylene glycol ether group or a combination of polyol group and polyglycol ether group. Such compounds are, for example, addition products of from about 4 to about 50 mol ethylene oxide and/or from about 0 to about 5 mol propylene oxide with linear and branched fatty alcohols, with fatty acids, and with alkyl phenols, in each case having from about 8 to about 20 C atoms in the alkyl group, ethoxylated mono-, di- and triglycerides, such as glycerol monolaurate+20 ethylene oxide, and glycerol monostearate+20 ethylene oxide, sorbitol fatty acid ester, and addition products of ethylene oxide with sorbitol fatty acid esters, such as Polysorbate (Tween 20, Tween 21, Tween 60, Tween 61, Tween 81), addition products of ethylene oxide with fatty acid alkanolamides and fatty amines, and alkylpolyglycosides. In particular, $C_8$-$C_{22}$ alkylmono- and -oligoglycosides and ethoxylated analogues thereof and also ethylene oxide addition products with saturated or unsaturated linear fatty alcohols each having from about 2 to about 30 mol ethylene oxide per mol of fatty alcohol are suitable as non-ionic surfactants.

Further oxidation compositions used with preference as contemplated herein are exemplified in that the at least one anionic surfactant is selected from alkyl sulfates, alkyl ether sulfates, and alkyl ether carboxylic acids each having from about 10 to about 18 C atoms, preferably from about 12 to about 14 C atoms in the alkyl group and up to about 12 glycolether groups, preferably from about 2 to about 6 glycol ether groups, in the molecule.

All cationic surface-active substances suitable for use on the human body are suitable in principle as cationic surfactants. These are exemplified by at least one water-soluble-making cationic group, such as a quaternary ammonium group, or by at least one water-soluble-making cationisable group, such as an amine group, and also at least one (lipophilically acting) alkyl group having from about 6 to about 30 C atoms or at least one (lipophilically acting) imidazole group or at least one (lipophilically acting) imidazyl alkyl group.

Agents that are preferred as contemplated herein contain at least one cationic surfactant, which is preferably selected from quaternary ammonium compounds having at least one C8-C24 alkyl group, esterquats and amidoamines each having at least one C8-C24 acyl group and mixtures hereof. Preferred quaternary ammonium compounds having at least one C8-C24 alkyl group are ammonium halides, in particular chlorides and ammonium alkyl sulfates, such as methosulfates or ethosulfates, such as C8-C24 alkyl trimethyl ammonium chlorides, C8-C24 dialkyl dimethyl ammonium chlorides and C8-C24 trialkyl methyl ammonium chlorides, for example cetyl trimethyl ammonium chloride, stearyl trimethyl ammonium chloride, distearyl dimethyl ammonium chloride, lauryl dimethyl ammonium chloride, lauryl dimethyl benzyl ammonium chloride, and tricetyl methyl ammonium chloride, and the imidazolium compounds known under the INCI names Quaternium-27, Quaternium-83, Quaternium-87 and Quaternium-91. The alkyl chains of the above-mentioned surfactants preferably have from about 8 to about 24 carbon atoms.

Esterquats are cationic surfactants which contain both at least one ester function and at least one quaternary ammonium group as structural element and also at least one C8-C24 alkyl group or C8-C24 acyl group. Preferred esterquats are quaternised ester salts of fatty acids with triethanolamine, quaternised ester salts of fatty acids with diethanol alkylamines and quaternised ester salts of fatty acids with 1,2-dihydroxypropyldialkylamines. Such products are sold for example under the trade name Stepantex®, Dehyquart® and Armocare®. N,N-bis(2-palmitoyloxyethyl)dimethyl ammonium chloride, Distearylethyl Dimonium Methosulfate and Distearoylethyl Hydroxyethylmonium Methosulfate are preferred examples of such esterquats.

The alkyl amidoamines are usually produced by amidation of natural or synthetic C8-C24 fatty acids and fatty acid sections with di-(C1-C3)alkyl amino amines. A compound from this substance group which is particularly suitable as contemplated herein is stearamidopropyl dimethylamine.

If not only a pure lightening or bleaching is desired, but also at the same time a change in the colour shade of the keratin fibres, the agents as contemplated herein can additionally also contain at least one substantive dye. These are dyes which are drawn directly onto the hair and do not require an oxidative process to form the colour.

To dull undesirable residual colour impressions caused by melanin degradation products, in particular in the red or blue spectrum, certain substantive dyes of the complementary colours are particularly preferably contained. Substantive dyes are usually nitrophenylenediamines, nitroaminophenols, azo dyes, anthraquinones or indophenols. Substantive dyes are known as anionic, cationic and non-ionic substantive dyes. The substantive dyes are each used preferably in an amount of from about 0.001 to about 2% by weight, in relation to the weight of the bleaching paste or the alkalising composition (Alk).

Preferred anionic substantive dyes are the compounds known under the international names or trade names Acid Yellow 1, Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1, Acid Black 52, bromophenol blue and tetrabromophenol blue. Preferred cationic substantive dyes include cationic triphenylmethane dyes, for example Basic Blue 7, Basic Blue 26, Basic Violet 2 and Basic Violet 14, aromatic systems which are substituted with a quaternary nitrogen group, for example Basic Yellow 57, Basic Red 76, Basic Blue 99, Basic Brown 16 and Basic Brown 17, cationic anthraquinone dyes, such as HC Blue 16 (Bluequat B), as well as substantive dyes containing a heterocyclic compound having at least one quaternary nitrogen atom, in particular Basic Yellow 87, Basic Orange 31 and Basic Red 51. The cationic substantive dyes sold under the Arianor trademark are likewise cationic substantive dyes preferred as contemplated herein. Suitable non-ionic substantive dyes are in particular non-ionic nitro and quinone dyes and neutral azo dyes. Preferred non-ionic substantive dyes are the compounds known under the international names or trade names HC Yellow 2, HC Yellow 4, HC Yellow 5, HC Yellow 6, HC Yellow 12, HC Orange 1, Disperse Orange 3, HC Red 1, HC Red 3, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4 and Disperse Black 9, and 1,4-diamino-2-nitrobenzene, 2-amino-4-nitrophenol, 1,4-bis (2-hydroxyethyl)amino-2-nitrobenzene, 3-nitro-4-(2-hydroxyethyl)aminophenol, 2-(2-hydroxyethyl)amino-4,6-dinitrophenol, 4-[(2-hydroxyethyl)amino]-3-nitro-1-methylbenzene, 1-amino-4-(2-hydroxyethyl) amino-5-chloro-2-nitrobenzene, 4-amino-3-nitrophenol, 1-(2'-ureidoethyl)amino-4-nitrobenzene, 2-[(4-amino-2-nitrophenyl)amino]benzoic acid, 6-nitro-1,2,3,4-tetrahydroquinoxaline, 2-hydroxy-1,4-naphthoquinone, picramic acid and salts thereof, 2-amino-6-chloro-4-nitrophenol, 4-ethylamino-3-nitrobenzoic acid, and 2-chloro-6-ethylamino-4-nitrophenol. A combination of tetrabromophenol blue and Acid Red 92 is contained very particularly preferably as contemplated herein.

As further optional ingredient, the agents as contemplated herein can contains at least one oxidation dye precursor product, which is preferably selected from one or more developer components and optionally one or more coupler components.

It may be preferred as contemplated herein to select, as developer component, at least one compound from the group formed from p-phenylenediamine, p-toluenediamine, 2-(2-hydroxyethyl)-p-phenylenediamine, 2-(1,2-dihydroxyethyl)-p-phenylenediamine, N,N-bis-(2-hydroxyethyl)-p-phenylenediamine, N-(4-amino-3-methylphenyl)-N-[3-(1H-imidazol-1-yl)propyl]amine, N,N'-bis-(2-hydroxyethyl)-N, N'-bis-(4-aminophenyl)-1,3-diaminopropan-2-ol, bis-(2-hydroxy-5-aminophenyl)methane, 1,3-bis-(2,5-diaminophenoxy)propan-2-ol, N,N'-bis-(4-aminophenyl)-1, 4-diazacycloheptane, 1,10-bis-(2,5-diaminophenyl)-1,4,7,10-tetraoxadecane, p-aminophenol, 4-amino-3-methylphenol, 4-amino-2-aminomethylphenol, 4-amino-2-(1,2-dihydroxyethyl)phenol, 4-amino-2-(diethylaminomethyl)phenol, 4,5-diamino-1-(2-hydroxyethyl)pyrazole, 2,4,5,6-tetraaminopyrimidine, 4-hydroxy-2,5,6-triaminopyrimidine, 2-hydroxy-4,5,6-triaminopyrimidine, and the physiologically acceptable salts thereof.

The agents as contemplated herein can contain at least one developer component in a total amount of from about 0.0001 to about 1.0% by weight, in each case in relation to the total weight of the agent. The agents as contemplated herein preferably contain one or more developer components in a total amount of from about 0.0001 to about 1.0% by weight, preferably from about 0.0001 to about 0.5% by weight, and particularly preferably from about 0.0001 to about 0.1% by weight.

Coupler components, within the scope of oxidative dyeing, do not alone form any significant colouration, but instead always require the presence of developer components. It is therefore preferred as contemplated herein for additionally at least one coupler component to be used when at least one developer component is used.

Coupler components that are preferred as contemplated herein are selected from 3-aminophenol, 5-amino-2-methylphenol, N-cyclopentyl-3-aminophenol, 3-amino-2-chloro-6-methylphenol, 2-hydroxy-4-aminophenoxyethanol, 2,6-dimethyl-3-aminophenol, 3-trifluoroacetylamino-2-chloro-6-methylphenol, 5-amino-4-chloro-2-methylphenol, 5-amino-4-methoxy-2-methylphenyl, 5-(2-hydroxyethyl)amino-2-methylphenol, 3-(diethylamino)phenol, N-cyclopentyl-3-aminophenyl, 1,3-dihydroxy-5-(methylamino)benzene, 3-ethylamino-4-methylphenol, 2,4-dichloro-3-aminophenol, diaminophenoxy)ethanol, 1,3-bis(2,4-diaminophenoxy)propane, 1-methoxy-2-amino-4-(2-hydroxyethylamino)benzene, 1,3-bis(2,4-diaminophenyl)propane, 2,6-bis(2'-hydroxyethylamino)-1-methylbenzene, 2-({3-[(2-hydroxyethyl)amino]-4-methoxy-5-methylphenyl}amino)ethanol, 2-({3-[(2-hydroxyethyl)amino]-2-methoxy-5-methylphenyl}amino)ethanol, 2-({3-[(2-hydroxyethyl)amino]-4,5-dimethylphenyl}amino)ethanol, 2-[3-morpholin-4-ylphenyl)amino]ethanol, 3-amino-4-(2-methoxyethoxy)-5-methylphenylamine, 1-amino-3-bis-(2-hydroxyethyl)aminobenzene, resorcinol, resorcinol monomethyl ether, 2-methylresorcinol, 5-methylresorcinol, 2,5-dimethylresorcinol, 2-chlororesorcinol, 4-chlororesorcinol, pyrogallol, 1,2,4-trihydroxybenzene, 2,6-dihydroxypyridine, 2-amino-3-hydroxypyridine, 2-amino-5-chloro-3-hydroxypyridine, 3-amino-2-methyl-amino-6-methoxypyridine, 2,6-dihydroxy-3,4-dimethylpyridine, 2,6-dihydroxy-4-methylpyridine, 2,6-diaminopyridine, 2,3-diamino-6-methoxypyridine, 3,5-diamino-2,6-dimethoxypyridine, 2,6-dihydroxy-3,4-dimethylpyridine, 3,4-diaminopyridine, 2-(2-methoxyethyl)amino-3-amino-6-methoxypyridine, 2-(4'-methoxyphenyl)amino-3-aminopyridine, 1-naphthol, 2-methyl-1-naphthol, 2-hydroxymethyl-1-naphthol, 2-hydroxyethyl-1-naphthol, 1,3-dihydroxynaphthalene, 1,5-dihydroxynaphthalene, 1,6-dihydroxynaphthalene, 1,7-dihydroxynaphthalene, 1,8-dihydroxynaphthalene, 2,7-dihydroxynaphthalene, 2,3-dihydroxynaphthalene, 4-hydroxyindole, 6-hydroxyindole, 7-hydroxyindole, 4-hydroxyindoline, 6-hydroxyindoline, 7-hydroxyindoline, 4-6-diaminopyrimidine, 4-amino-2,6-dihydroxypyrimidine, 2,4-diamino-6-hydroxypyrimidine, 2,4,6-trihydroxypyrimidine, 2-amino-4-methylpyrimidine, 2-amino-4-hydroxy-6-methylpyrimidine and 4,6-dihydroxy-2-methylpyrimidine or mixtures of these compounds or the physiologically acceptable salts thereof.

The agents as contemplated herein can contain at least one coupler component in a total amount of from about 0.0001 to about 10.0% by weight, in each case in relation to the total weight of the agent. The agents as contemplated herein preferably contain one or more coupler components in a total amount of from about 0.0001 to about 1.0% by weight, preferably from about 0.0001 to about 0.5% by weight, and particularly preferably from about 0.0001 to about 0.1% by weight.

Method

A second subject of the present disclosure is a method for the oxidative changing of the colour of hair, comprising the following steps in the specified order:

(I) producing a ready-to-use agent by mixing, with water, an agent as was described in detail in the description of the first subject of the present disclosure;

(II) applying the ready-to-use agent produced in step (I) to the hair;

(III) leaving the agent to take effect; and (IV) rinsing out the agent from the hair.

What is particularly preferred is a method for lightening or bleaching hair comprising the following steps in the specified order:

(I) producing a ready-to-use agent by mixing, with water, an agent as was described in detail in the description of the first subject of the present disclosure;

(II) applying the ready-to-use agent produced in step (I) to the hair;

(III) leaving the agent to take effect; and (IV) rinsing out the agent from the hair.

Within the scope of a particularly well-suited embodiment, the agent forming the first subject of the present disclosure for example can be provided in a container, a bottle or a can. Here, the dimensions of the container can be selected such that the container is only partially filled and can be filled further with water. The amount of water that must then be added to produce the ready-to-use agent can be defined for example by a marking on the wall of the container. The application mixture is produced by adding the corresponding amount of water and for example shaking the container.

Within the scope of a further embodiment the agent as contemplated herein can also be provided in a sachet, a pouch, a can or another storage container. In order to produce the ready-to-use agent, the user then transfers the sachet (or the like) entirely into a bowl, glass or vessel and then adds the recommended amount of water—whilst shaking or stirring.

The mixing ratio of agent as contemplated herein to water can be, for example from about 1:3 (1 part by weight agent as contemplated herein to 3 parts by weight water) to about 3:1, preferably from about 1:2 to about 2:1.

The ready-to-use mixtures formed of the agent and water preferably have a viscosity in the range of from about 3000 to about 40000 mPas, preferably from about 4000 to about 30000 mPas, particularly preferably from about 6000 to about 15000 mPas, in each case measured at 20° C. with a Haake cylinder/cylinder viscometer, rotary/measurement system SV I with a cooling time of about 5 minutes. In this measurement method the viscosity value is determined at a shear rate of 1/7.2 s. The measurement program operates with a ramp of 0-1/60 s. A viscosity in this range makes it possible for the ready-to-use agent to be easily applied, and also to have flow behaviour such that it guarantees a sufficiently long reaction time for the agent on the keratin fibres at the target site.

The reaction time in step (III) of the method as contemplated herein is preferably from about 5 to about 60 min., in particular from about 5 to about 50 min., particularly preferably from about 10 to about 45 min. During the reaction time of the agent on the fibres, it may be advantageous to assist the colour changing process by supplying heat. A reaction phase at room temperature is also included as contemplated herein. In particular, the temperature during the reaction time lies between about 20° C. and about 40° C., in particular between about 25° C. and about 38° C. The agents demonstrate good treatment results already at physiologically acceptable temperatures of less than about 45° C.

Following the end of the colour changing process, all components on the keratin fibres are rinsed from the hair using water or a surfactant-containing cleansing agent. Cleansing agents may be in particular commercially available shampoos, wherein in particular it may be possible to dispense with the cleansing agent and to perform the rinse-out process using mains water of the colour-changing agent has a higher surfactant content.

That said in respect of the agents as contemplated herein applies, mutatis mutandis also for the methods as contemplated herein.

EXAMPLES

1. Formulations

The following formulations were produced (unless specified otherwise, the specified amounts correspond to % by weight).

Bleaching Powder

|  | Ex. 1 I | Ex. 2 I | Ex. 3 C | Ex. 4 C |
|---|---|---|---|---|
| Ammonium persulfate | 10.0 | 10.0 | 10.0 | 10.0 |
| Potassium persulfate | 28.0 | 28.0 | 28.0 | 28.0 |
| Sodium persulfate | 2.0 | 2.0 | 2.0 | 2.0 |
| Sodium silicate (molar ratio SiO2/Na2O = 2.5) | 28.0 | 28.0 | 28.0 | 28.0 |
| Methyl methacrylate, methacrylic acid Copolymer (Degalan RG S hv, Evonic) | 1.0 | 1.0 | 1.0 | 1.0 |
| Carboxymethyl cellulose (Na salt) (Cekol 50000, CP Kelco) | 1.5 | 1.5 | 1.5 | 1.5 |
| Hydroxyethylcellulose (Natrosol 250 HR, Ashland) | 2.5 | 2.5 | 2.5 | 2.5 |
| Silica, hydrophilic | 0.2 | 0.2 | 0.2 | 0.2 |
| Polyquaternium-4 | 0.3 | 0.3 | 0.3 | 0.3 |
| EDTA, Tetrasodium salt | 1.6 | 1.6 | 1.6 | 1.6 |
| Sodium percarbonate | 4.0 | 8.0 | 16.0 | 24.0 |
| Magnesium carbonate | to 100 | to 100 | to 100 | to 100 |

I = as contemplated herein
C = comparison

2. Application

Each bleaching powder was mixed with water in a ratio 1:2 (1 part by weight bleaching powder with 2 parts by weight water). The ready-to-use bleaching agents obtained in this way were each applied to hair strands (Fischbach & Miller, light brown) and left to take effect for 45 minutes. The hair strands were then washed using a commercially available shampoo and water.

Each hair strand was measured colorimetrically before and after the bleaching (spectrophotometer from the company Datcolor, SF450). The colour distance (dE value) was determined from the Lab values obtained during the measurements.

3. Bleaching Power

|  | L | a | b | dE value |
|---|---|---|---|---|
| before bleaching | 23.75 | 6.64 | 10.78 | — |
| Ex. 1 E | 43.58 | 10.72 | 25.50 | 25.03 |
| Ex. 2 E | 43.91 | 11.38 | 26.93 | 26.26 |
| Ex. 3 C | 43.35 | 10.14 | 25.10 | 24.52 |
| Ex. 4 C | 43.33 | 10.42 | 25.60 | 24.85 |

The L-value indicates the brightness of the colouring (L=0, black; L=100, white). The higher is the L-value of the treated strands, the greater was the bleaching of the strands.

The ΔE value used for the assessment of the colour intensity is given from the L*a*b* colorimetric values as follows:

$$\Delta E = [(L_i - L_0)^2 + (a_i - a_0)^2 + (b_i - b_0)^2]^{1/2}$$

$L_0$, $a_0$ and $b_0$: Colorimetric values before the bleaching
$L_i$, $a_i$ and $b_i$: Colorimetric values after the bleaching The ΔE value indicates the colour difference between the untreated and the treated hair strands. The greater is the dE value, the greater is the colour difference (i.e. the colour distance) between the uncoloured and the coloured hair, and the stronger is the bleaching power.

4. Measurement of the Cysteic Acid Content

In order to measure the hair damage caused by the bleaching, the cysteic acid value of each treated hair strand was determined by employing quantitative NIR spectroscopy.

The spectra were recorded using an MPA™ $^{FT}$-NIR spectrometer from the company Bruker Optik GmbH. The infrared range comprises the wave number range of from 12500 cm$^{-1}$ to 4000 cm$^{-1}$ and is characteristic for overtone and combination vibrations of, for example, CH, OH and NH groups.

The measurement of the samples was performed with the integration bead module on six different sample positions in diffuse reflection. The wave number range of from 7300 cm$^{-1}$ to 4020 cm$^{-1}$ was selected for the analysis of the measured NIR spectra.

The NIR spectra of cystine in the wave number range of from 6200 cm$^{-1}$ to 5500 cm$^{-1}$ represent characteristic absorption bands. If the hair changes due to more severe damage (i.e. the cysteic acid content in the hair increases), this has an effect in the NIR spectrum on the bands at 5020 cm$^{-1}$ to 4020 cm$^{-1}$ characteristic for cysteic acid. The quantitative evaluation of the NIR spectra was performed in a computer-assisted manner.

NIR analysis value [mol cysteic acid/100 mol amino acid]

|  | Untreated hair strands | Ex. 1 I | Ex. 2 I | Ex. 3 C | Ex. 4 C |
|---|---|---|---|---|---|
| mol cysteic acid/100 mol amino acid | 0.8 | 1.4 | 1.5 | 1.8 | 1.9 |

Hair strands that were treated with the agents (I) as contemplated herein had a reduced cysteic acid value compared to the comparison formulation (V) and thus sustained a lower amount of hair damage.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. An anhydrous bleaching powder for the oxidative changing of the colour of keratin fibres, comprising—in relation to its total weight—
   (a) from about 0.5 to about 14.0% by weight of sodium percarbonate
   (b) 10.0% by weight of ammonium persulfate
   (c) 28.0% by weight of potassium persulfate
   (d) 2.0% by weight of sodium persulfate
   (e) from about 0.75 to about 1.5% by weight of methyl methacrylate, methacrylic acid copolymer
   (f) from about 1 to about 5% by weight of hydroxy ethyl cellulose and sodium carboxy methyl cellulose.

2. A method for the oxidative changing of the colour of hair, comprising the following steps in the specified order:
   (I) producing a ready-to-use agent by mixing, with water, an anhydrous bleaching powder according to claim 1;
   (II) applying the ready-to-use agent produced in step (I) to the hair;
   (III) leaving the agent to take effect; and
   (IV) rinsing out the agent from the hair.

* * * * *